(12) United States Patent
Polcawich et al.

(10) Patent No.: US 7,304,732 B1
(45) Date of Patent: Dec. 4, 2007

(54) MICROELECTROMECHANICAL RESONANT PHOTOACOUSTIC CELL

(75) Inventors: Ronald G. Polcawich, Derwood, MD (US); Paul Pellegrino, Columbia, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 402 days.

(21) Appl. No.: 10/716,748

(22) Filed: Nov. 19, 2003

(51) Int. Cl.
*G01N 21/00* (2006.01)

(52) U.S. Cl. ............... 356/246; 250/339.07; 422/82.09; 73/61.45

(58) Field of Classification Search ............... 356/244, 356/246, 432–444; 73/61.45, 24.04, 61.49; 250/339.07, 339.08, 343; 422/82.09, 102
See application file for complete search history.

(56) References Cited

U.S. PATENT DOCUMENTS

| | | | |
|---|---|---|---|
| 3,820,901 A | 6/1974 | Kreuzer | |
| 4,028,932 A * | 6/1977 | Rosencwaig ............... | 73/579 |
| 4,096,626 A * | 6/1978 | Olsen et al. ............... | 29/846 |
| 4,163,382 A | 8/1979 | Amer | |
| 4,436,428 A * | 3/1984 | Watanabe et al. ........... | 356/432 |
| 4,761,381 A * | 8/1988 | Blatt et al. ................ | 436/165 |
| 4,947,859 A | 8/1990 | Brewer et al. | |
| 5,110,727 A * | 5/1992 | Oberhardt ................. | 435/13 |
| 5,129,262 A * | 7/1992 | White et al. ............... | 73/599 |
| 5,283,037 A | 2/1994 | Baer et al. | |
| 5,559,358 A * | 9/1996 | Burns et al. .............. | 257/431 |
| 5,910,286 A | 6/1999 | Lipskier | |
| 6,033,852 A | 3/2000 | Andle et al. | |
| 6,116,080 A | 9/2000 | Logue et al. | |
| 6,161,437 A | 12/2000 | Brennan et al. | |
| 6,188,474 B1 * | 2/2001 | Dussault et al. ............ | 356/246 |
| 6,236,455 B1 | 5/2001 | Autrey et al. | |
| 6,244,101 B1 * | 6/2001 | Autrey et al. .............. | 73/61.45 |
| 6,286,360 B1 * | 9/2001 | Drzewiecki ................ | 73/24.01 |
| 6,344,647 B1 * | 2/2002 | Jourdain et al. ........ | 250/339.07 |
| 6,348,968 B2 * | 2/2002 | Autrey et al. ............... | 356/432 |
| 6,552,792 B1 | 4/2003 | Pilgrim et al. | |
| 6,600,558 B2 * | 7/2003 | Ueno et al. ................. | 356/246 |
| 6,608,683 B1 * | 8/2003 | Pilgrim et al. ............. | 356/432 |
| 6,870,626 B2 * | 3/2005 | Autrey et al. ............... | 356/432 |
| 7,034,943 B1 * | 4/2006 | Moeckli et al. ............. | 356/423 |
| 2002/0176804 A1 | 11/2002 | Strand et al. | |

\* cited by examiner

*Primary Examiner*—Sang H Nguyen
(74) *Attorney, Agent, or Firm*—Edward L. Stolarun; William W. Randolph; A. David Spevack

(57) ABSTRACT

An integrated photoacoustic spectroscopy (PAS) cell is fabricated using microelectromechanical (MEMS) techniques. The multi-layer structure includes an inner layer with a patterned resonant cavity disposed between top and bottom outer layers and a microphone acoustically coupled to the resonant cavity. In the preferred embodiment, the microphone is a piezoelectric thin-film membrane formed on one of the outer layers. The inner layer is additionally patterned to include buffer cavities on either side of the resonant cavity, and one or both of the top and bottom outer layers are also patterned to include buffer cavities aligned with the buffer cavities in the inner layer on either side of the resonant cavity. The preferred fabrication method involves joining an inner silicon substrate to a pair of outer silicon substrates, thereby encapsulating the resonant cavity, and depositing a piezoelectric thin film onto one of the outer substrates which is then patterned to create an acoustic sensor.

3 Claims, 1 Drawing Sheet

MICROELECTROMECHANICAL RESONANT PHOTOACOUSTIC CELL

GOVERNMENT INTEREST

The invention described herein may be manufactured, used, and licensed by or for the United States Government.

FIELD OF THE INVENTION

This invention relates generally to photoacoustic spectroscopy (PAS) and, in particular, to the fabrication, assembly, and use of a microelectromechanical (MEMS) resonant acoustic cavity and piezoelectric microphone for photoacoustic spectroscopy.

BACKGROUND OF THE INVENTION

Broadly, photoacoustic spectroscopy (PAS) is a detection method based on several simple principles: 1) the absorption of light by an analyte molecule; 2) the subsequent generation of an acoustical wave generated by the molecular relaxation, and 3) the detection of the acoustic wave by a pressure sensing device (e.g., a microphone).

The basic photoacoustic effect was discovered over a century ago. A. G. Bell, *Proc. Am. Assoc. Adv. Science*, Vol. 29, page 115 (1880), *Phil Mag.* Vol. 11, page 510 (1881; J. Tyndall, *Proc. Roy. Soc.* Vol. 31, page 307 (1881); and W. C. Rontgen, *Phil. Mag.* Vol. 11, page 308 (1881) discovered the opto-acoustic effect and its use in the "spectrophone." Briefly, input optical radiation, periodically interrupted at a frequency in the audible range, was directed upon a gas medium in a glass container; and the periodic pressure fluctuations resulting from the absorption of radiation by the gas was detected by ear through a listening tube connected to the container. Other background references of interest include U.S. Pat. Nos. 3,700,890, issued Oct. 24, 1972 and 3,820,901 issued Jun. 28, 1974, each in the name of L. B. Kreuzer; L. B. Kreuzer, *J. Appl. Phys.* 42, 2934 (1971); C. F. Dewey et al, *Appl. Phys. Letters* 23, 633 (1973); R. D. Kamm, *J. Appl. Phys.* 47, 3550 (1976); E. Max et al, *Opt. Comm.* 11, 422 (1974); and C. K. Patel et al, *Appl. Phys. Letters* 30, 578 (1977).

To this day, most photoacoustic cells are macro-scale devices measuring from inches to upward of a meter in length. The basic designs consist of a light source and a sealed cell including gas inlets and outlets, transparent windows, and a sensing microphone. In the past, the optical radiation was provided by an assortment of light sources including lamps, lasers, light-emitting diodes (LED) and even blackbodies. Although some modern trace gas measurement instruments based on photoacoustics utilize lamps, the majority of recent research for trace gas sensing in photoacoustics has been dominated by the use of laser sources. In particular, lasers sources have allowed the added advantage of increased modulation capabilities (up to GHz levels) not possible with other sources. Most thermal sources modulated through alternating current only maintain full modulation depth at low frequency (<100 Hz). Even with mechanical modulation (chopper wheel) of these sources, the highest possible modulation is still modest (<6.4 kHz).

In order to increase sensitivity of the photoacoustic signals, the modulation of the light source is designed to correspond to the acoustic resonant frequency in the photoacoustic cell in order to amplify generated acoustic signals. The lowest order mode that could be acoustically resonated in such a structure would correspond to the first longitudinal mode given by $\omega_{res}=c/2l_{res}$, where $\omega_{res}$ is the acoustic frequency, c is the speed of sound, and $l_{res}$ is the resonator length. Resonant photoacoustic cells designed to take advantage of typical MEMS processing would practically have resonant structures on the order of one to several millimeters in length. Assuming atmospheric pressure, ambient temperature, and the resonator lengths suggested above implies an optical radiation source would have to modulated at approximately 10-100 KHz level to drive the photoacoustic cell into acoustic resonance. These requirements exclude the use of any thermal source necessitating the use of either a laser or LED.

Some described devices employ other features to improve sensitivity such as multiple-sensing microphones, resonant acoustic cavities, noise-suppression volumes, turntable light sources and multi-light-pass arrangements. As an example of one improvement, U.S. Pat. No. 4,163,382 discloses a method and apparatus that increases the sensitivity and flexibility of laser optocaustic spectroscopy, with reduced size. According to the method, it was longer as necessary to limit the use of laser optocaustic spectroscopy to species whose absorption must match available laser radiation. Instead, "doping" with a relatively small amount of an optically absorbing gas yields optocaustic signatures of non-absorbent materials (gases, liquids, solids, and aerosols), thus significantly increasing the sensitivity and flexibility of opt caustic spectroscopy.

Another improvement to PAS, called wavelength modulated photoacoustic spectroscopy, or WM-PAS, eliminates a major noise source associated with traditional implementations of PAS. WM-PAS has been practiced in the prior art. An early description of the technique was provided by C. F. Dewey, *Optoacoustic Spectroscopy and Detection*, (Y-H Pao, ed., Academic Press, New York, 1977), pp. 62-64. Others have since practiced the technique including M. Feher, et al., *Applied Optics* 33, 1655 (1994); A. Miklos, et al., *Applied Physics B* 58, 483 (1994); and B. E. R. Olsson, et al., *Applied Spectroscopy* 49, 1103 (1995). All use sinusoidal wavelength modulation waveforms. U.S. Pat. No. 6,552,792 improves on traditional sinusoidal modulation through the use of a modified square wave to provide increased signal compared to the sinusoidal and triangle waveforms.

Although sensitive, these devices have several shortcomings, including the large size of the cell and other apparatus. Accordingly, there exists the need for a trace chemical sensor, preferably with high-sensitivity, low-cost, low power consumption, and the capability to be mass-produced.

SUMMARY OF THE INVENTION

This invention improves upon the existing art by providing an integrated photoacoustic spectroscopy (PAS) cell fabricated using microelectromechanical (MEMS) techniques. The device is broadly based on a multi-layer structure including an inner layer disposed between top and bottom outer layers, with the inner layer being patterned to include a resonant cavity, and a microphone acoustically coupled to the resonant cavity.

In the preferred embodiment, the microphone is a piezoelectric thin film membrane formed on one of the outer layers. The resonant cavity is an open-tube resonant cavity to receive light from a source, and the inner layer is additionally patterned to include buffer cavities on either side of the resonant cavity. One or both of the top and bottom outer layers are patterned to include buffer cavities aligned with the buffer cavities in the inner layer on either side of the resonant cavity.

The preferred fabrication method involves joining an inner silicon substrate to a pair of outer silicon substrates, thereby encapsulating the resonant cavity, and depositing a piezoelectric thin film onto one of the outer substrates which is then patterned to create an acoustic sensor. The piezoelectric thin film may be any useful material, including lead zirconate titanate (PZT), aluminum nitride (AlN), or zinc oxide (ZnO). The resonant cavity and buffer cavities are formed using deep etch techniques subsequent to appropriate masking. The step of joining the inner substrate to the outer substrates preferably uses temperature and pressure to create a gold-silicon or gold-tin hermetic bond.

BRIEF DESCRIPTION OF THE INVENTION

Figure 1:
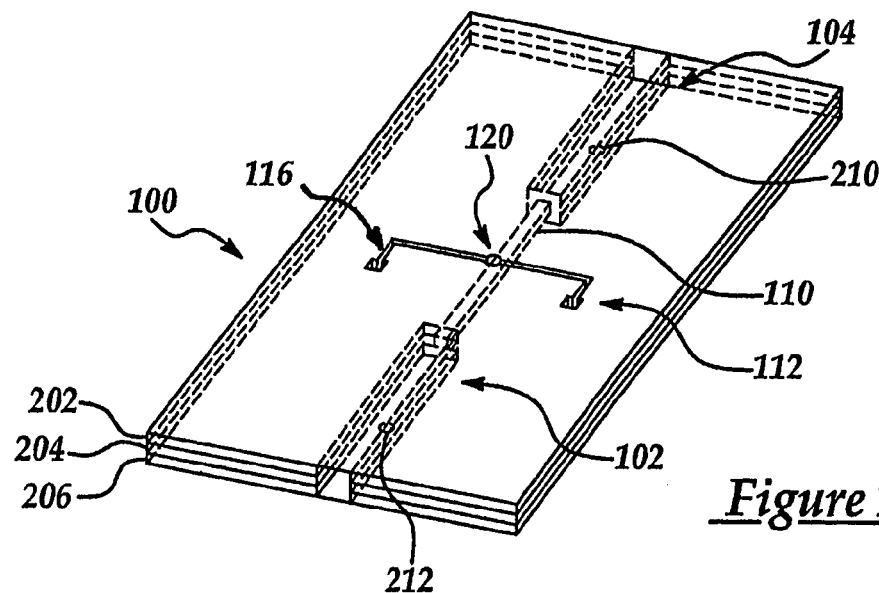
FIG. 1 is a perspective view of an assembled photoacoustic spectroscopy cell constructed in accordance with the preferred embodiment of this invention.
Figure 2:
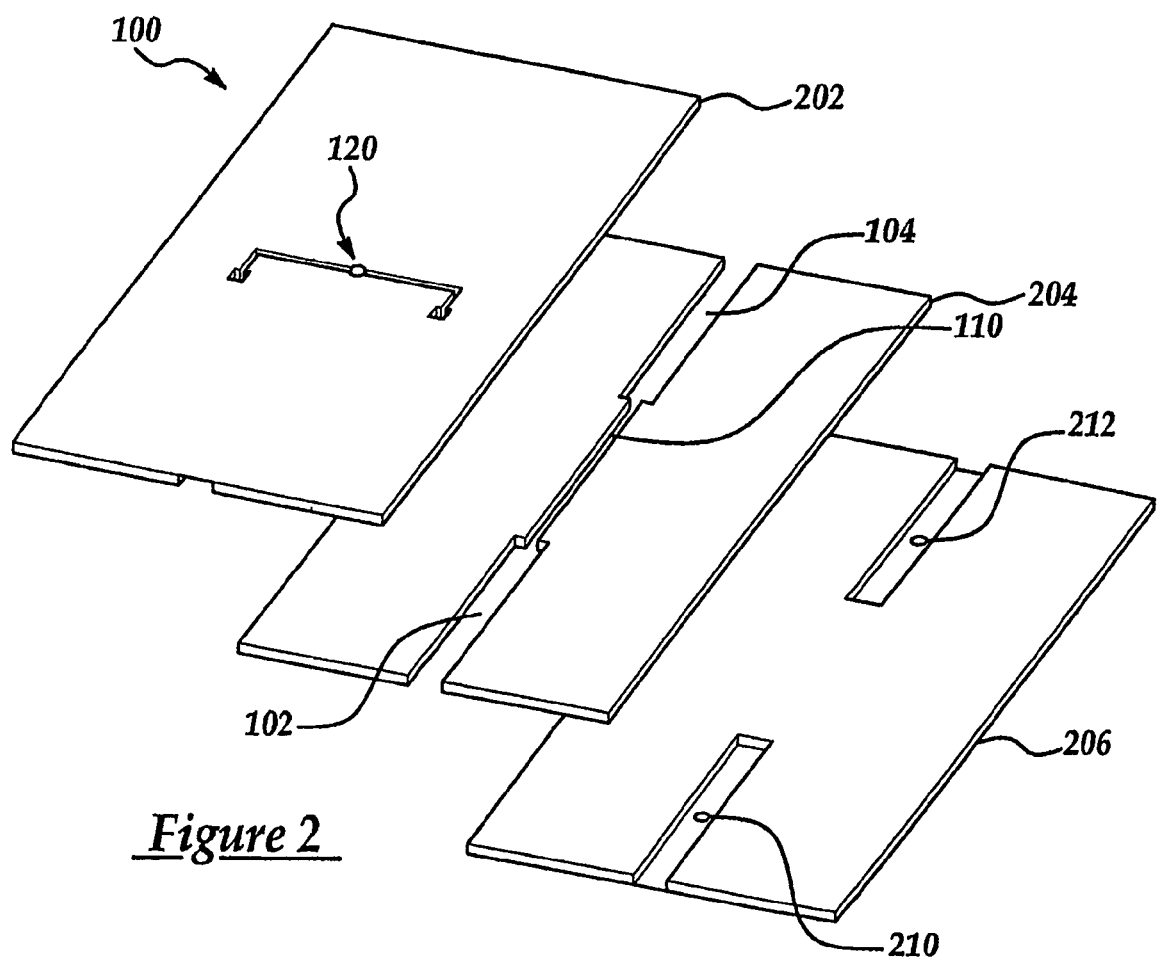
FIG. 2 is an exploded view of the photoacoustic spectroscopy cell of FIG. 1 showing important component layers.

This invention resides in the fabrication, assembly, and use of a microelectromechanical (MEMS) resonant acoustic cavity and microphone for photoacoustic spectroscopy. The fabrication process involves a three-wafer process with the final structure utilizing wafer bonding for assembly.

Referring now to the Figures, an inventive resonant photoacoustic spectroscopy cell is shown generally at 100. The resonant cell 100 includes a fore buffer volume cavity 102, and an aft buffer volume cavity 104 that serve as buffer regions to suppress spurious acoustic inputs. The cell 100 also includes a central open tube resonant cavity 110.

The top wafer 202 of the resonant cell 100 encompasses portions of both the fore cavity 102 and the aft cavity 104 and the acoustical channel 120 from the resonant cavity 110. A thin film piezoelectric membrane, generally shown as 112, is deposited on the top wafer (see Step 4 in Top Wafer Process, paragraphs 0019-0031 supra). The portion of the thin film piezoelectric membrane 112 overlaying the acoustical channel 120 operates as an acoustic sensor or piezoelectric microphone and the terms are used synonymously herein. Electrical contacts 116 are connected to the top and bottom surfaces of the thin film piezoelectric membrane 112 and provide a means of transferring the piezoelectrically generated voltage from the top wafer to external digital signal processing equipment (not shown). The inner wafer 204 creates the central resonant cavity 110 and defines a portion of the fore cavity 204 and aft cavity 104. The bottom wafer 206 forms the remaining volumes of both buffer cavities 102 and 104 and gas input via port 210 and gas via output port 212 that are in fluid communication with central resonant cavity 110 as well as the buffer cavities 102 and 104. The resonant cavity 110 is formed to allow the interaction of a light source with the medium of interest with the cavity volume.

The processing of the various wafers to form an inventive cell follows according to a preferred embodiment. It is appreciated that the relative position of inventive cell element is variable and still affords an operative cell. Additionally, it is appreciated that optional further wafer layers are readily incorporated into an inventive cell. Further wafer laminates are appreciated to illustratively afford more complex resonant cavity shapes, introduce additional sensor elements, introduce additional gas via ports, introduce baffles or acoustic dampers, and the like.

Top Wafer Process
1. Starting wafer is double-sided polished silicon substrate.
2. Deposition of silicon dioxide on top surface either through low-pressure chemical vapor deposition (LPCVD), plasma enhanced chemical vapor deposition (PECVD), or thermal oxidation.
3. Deposition of titanium/platinum or tantalum/platinum thin films on top surface.
4. Deposition of piezoelectric thin film either lead zirconate titanate (PZT) or aluminum nitride (AlN) onto top surface.
5. Deposition of platinum onto top surface and patterning of platinum via metal lift-off technique.
6. Deposition of PECVD silicon dioxide onto back of substrate.
7. Pattern piezoelectric thin film by reactive ion etching or ion-milling.
8. Deposition of PECVD silicon dioxide onto top surface to serve as passivation layer.
9. Pattern silicon dioxide layer of Step 8 with reactive ion etching.
10. Deposition of titanium/gold for electrical contacts on top surface and use lift-off technique for contact patterning.
11. Deposition of titanium/gold or gold-tin on back of substrate (use lift-off technique for pattern definition).
12. Pattern silicon dioxide on back of substrate via reactive ion etching.
13. Pattern silicon on back of substrate via silicon deep reactive ion etching to form buffer regions and the acoustical channel to thereby form the piezoelectric thin film membrane across the top of the acoustic channel which is operable as the piezoelectric microphone.

Inner Wafer Process
1. Starting wafer is double-sided polished silicon substrate.
2. Deposition of titanium/gold or gold-tin onto both surfaces of substrate (use liftoff technique for pattern definition).
3. Etch resonant cavity and buffer regions using silicon deep reactive ion etching.

Bottom Wafer Process
1. Starting wafer is double-sided polished silicon substrate.
2. Pattern silicon on back surface with reactive ion etching to form gas via ports.
3. Deposition of titanium/gold or gold-tin on back of substrate (use liftoff technique for pattern definition).
4. Pattern silicon on front surface with deep reactive ion etching to form buffer regions and via ports.

Die Assembly
1. Use aluminum die aligner for properly aligning all components.
2. Use temperature and pressure to create a gold-silicon or gold-tin eutectic bond between the components.

Completing Photoacoustic Resonant Cell
1. Attach focusing optics to the front buffer region.
2. Attach microtubing to the gas input and output ports.

The piezoelectric MEMS-based photoacoustic cell combines the advantages of MEMS fabrication and piezoelectric sensing. An advantage of the present invention is the reduction in component volume. With a reduction in size in the present invention, the piezoelectric microphone is closer to the acoustic source than conventional devices. This proximity increases signal strength and overall sensitivity of the inventive cell. Additionally, the inventive photoacoustic cell is constructed solely on the MEMS scale including gas inlets/outlets, sensing microphone(s), noise suppression volumes, and resonant cavity all located in a monolithic MEMS package. MEMS are manufactured in a large-scale batch-type fabrication, which inherently lower the cost of the final product. Additionally, the processing can be extremely accurate with tolerances generally more accurate than one micron. Piezoelectric sensing is extremely attractive for miniature components because it is a high-efficiency conversion of mechanical to electrical energy and a passive sensing technique, i.e. does not require an electrical power source. The technology incorporated in the inventive photoacoustic cell makes photoacoustic spectroscopy as a handheld technique viable for numerous commercial and military chemical-sensing requirements.

The invention is applicable to all types of gas sensing and monitoring, including industrial waste gas monitoring, chemical detection on the battlefield, etc. Although the main use of photoacoustics is in trace gas sensing, the application can be used to detect absorption events in any phase gas, liquid or solid while avoiding effects from scattering phenomenon. This could make the technique viable for other ancillary markets. Additionally, there are several uses for the piezoelectric microphone itself that include passive acoustic detection for the military and physiological sensors for biological diagnostics.

Additionally, since this invention resides in a basic cell design, the application may take advantage of any additional or peripheral photoacoustic spectroscopy apparatus or methods, whether existing or yet-to-be-developed, including integrated versus discrete window technologies; optical tuning, chopping or modulation techniques; multi-light-pass arrangements; comparisons to reference cells; multiple sensing microphones, including thin-film approaches; and so forth.

We claim:

1. A method of fabricating a photoacoustic spectroscopy cell formed of top, bottom and inner substrates, comprising the steps of:

forming a resonant cavity and buffer cavities on either side of the resonant cavity in the inner substrate;

joining the inner substrate to a pair of top and bottom outer substrates, thereby encapsulating the resonant cavity;

acoustically coupling a microphone to the resonant cavity; and wherein the substrates are silicon and the step of acoustically coupling a microphone to the resonant cavity includes the steps of:

depositing a piezoelectric thin film onto one of the top and bottom substrates;

etching and patterning the thin film to create an acoustic sensor; and forming a port extending from the acoustic sensor into the resonant cavity.

2. The method of claim 1, wherein the substrates are silicon material coated with one of titanium-gold or tin-gold alloy and further including the step of compressing the substrates together and using temperature and pressure to form a gold-silicon or gold-tin eutectic bond between the substrates.

3. The method of claim 1 wherein the piezoelectric thin film is selected from the group of lead zirconate titanate (PZT), aluminum nitride (AlN), and zinc oxide (ZnO).

* * * * *